United States Patent [19]
Strobel

[11] 3,931,261
[45] Jan. 6, 1976

[54] BROMOSALICYLANILIDE BIOCIDAL AGENTS

[75] Inventor: Albert F. Strobel, Delmar, N.Y.

[73] Assignee: GAF Corporation, New York, N.Y.

[22] Filed: Sept. 17, 1971

[21] Appl. No.: 181,560

[52] U.S. Cl. .......... 260/429.9; 260/438.1; 260/509; 424/230
[51] Int. Cl.$^2$ .......................................... C07F 3/06
[58] Field of Search .......... 260/429.9, 438.1, 559 S, 260/509

[56] References Cited
UNITED STATES PATENTS

| | | | |
|---|---|---|---|
| 3,057,920 | 10/1962 | Schramm | 260/559 S |
| 3,064,048 | 11/1962 | Schramm | 260/559 S |

FOREIGN PATENTS OR APPLICATIONS

| | | |
|---|---|---|
| 139,508 | 11/1960 | Japan |

OTHER PUBLICATIONS
Chemical Abstracts, Vol., p. 12373, (1964).
Chemical Abstracts, Vol. 58, pp. 2675–2677, (1963).
Chemical Abstracts, Vol. 66, pp. 115475p, (1967).
Chemical Abstracts, Vol. 68, p. 12731f, (1968).

*Primary Examiner*—Helen M. S. Sneed
*Attorney, Agent, or Firm*—Walter C. Kehm

[57] ABSTRACT

Biocidal agents, such as bactericides and fungicides, are bromosalicylanilide derivatives of the following formula:

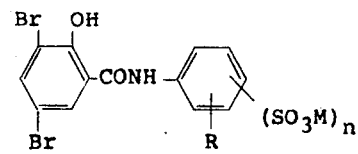

wherein R is hydrogen or a halogen atom such as chlorine or bromine, $n$ is a whole number of 1 or 2 and M is a metal salt such as an alkali metal, alkaline earth metal, copper or zinc. These compounds are prepared by reaction of a 3,5-dibromosalicylic acid halide with the desired aminobenzenesulfonic acid.

9 Claims, No Drawings

BROMOSALICYLANILIDE BIOCIDAL AGENTS

BACKGROUND OF THE INVENTION

1. Field of the Invention

This invention relates to novel bromosalicylanilide derivatives which are useful as biocidal agents and particularly useful as fungicides and bactericides.

2. Description of the Prior Art

It is known in the prior art that certain brominesubstituted salicylanilide compounds are useful in the biocidal area. For example, di- and tri-bromosalicylanilides are described in U.S. Pat. No. 2,906,711 as being useful as germicides. Further, U.S. Pat. No. 3,041,236 discloses that dibromo salicylanilides containing a trifluoromethyl group are bactericides. Also, British Pat. No. 840,366 discloses 3,4',5-tribromosalicylanilide as useful in germicidal preparations. In general, these halogenated salicylanilides are prepared by halogenation of the corresponding salicylanilide compounds as disclosed in these references. However, as indicated in these patents the halogenation process of the prior art generally result in the preparation of only mixtures of products which comprise isomeric halogenated products having varying degrees of halogenation. This is illustrated for example by U.S. Pat. No. 2,967,885 which describes a method for bromination of salicylanilide where it is specifically indicated that by suitable control of the reaction, a major portion of the product is 3,4',5-tribromosalicylanilide but that other products, including 3,5- and 4',5-dibromosalicylanilides and 2',3-,4',5-tetrabromosalicylanilide are also produced in the process. Hence only mixtures are obtained. Therefore, while the prior art has recognized that dibromosalicylanilides do exhibit biocidal properties the art has not disclosed suitable procedures by which these compounds can be prepared in high purity. Further, the art has not disclosed processes for preparation of compounds of this type which contain sulfonic acid groups and therefore are watersoluble for wider use areas.

SUMMARY OF THE INVENTION

It is accordingly one object of this invention to provide dibromosalicylanilide derivatives which contain sulfonic acid groups, which salicylanilides have biocidal properties, especially in the fungicidal and bactericidal area.

A further object of this invention is to provide 3,5-dibromosalicylanilide derivatives and compositions useful as fungicides and bactericides, which salicylanilides contain sulfonic acid groups on the aniline moiety of the molecule.

A still further object of the invention is to provide sulfonic acid substituted dibromosalicylic acid derivatives which are water-soluble and thus can be dissolved in aqueous solutions without requirements for dispersement, which compositions exhibit a higher degree of mildew-proofing characteristics than the corresponding non-sulfonated derivatives.

A still further object of this invention is to provide a method of preparation for the compounds as well as compositions and methods for their use as biocidal materials.

Other objects and advantages of the present invention will become apparent as the description thereof proceeds.

In satisfaction of the foregoing objects and advantages there are provided by this invention novel bromosalicylanilide derivatives which have the following structural formula:

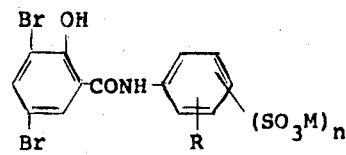

wherein R is hydrogen or a halogen atom such as chlorine or bromine, $n$ is a whole number of 1 or 2, M is a metal salt such as an alkali metal, an alkaline earth metal, copper or zinc. Also provided are compositions and methods for using these compounds as fungicidal and bactericidal materials as well as procedures for preparation of the compounds by reaction of the 3,5-dibromosalicylic acid halide with the corresponding aminobenzenesulfonic acid.

DESCRIPTION OF PREFERRED EMBODIMENTS

As indicated above, the present invention provides novel bromosalicylanilide derivatives which have been found to be useful as biocidal compounds, particularly as fungicides and bactericides. The compounds of this invention are salicylanilide derivatives and may best be defined by the following structural formula:

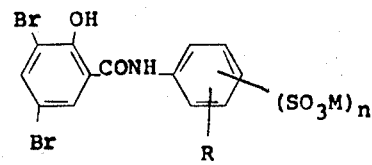

wherein R is hydrogen or a halogen atom such as chlorine or bromine, $n$ is a whole number of 1 or 2 and M is a metal salt such as an alkali metal, for example sodium, potassium, an alkaline earth metal such as calcium, magnesium, as well as copper and zinc. In the above formula, it will be understood that when the metal representing M is divalent, it will be attached to two molecules through the $SO_3H$ group. In specific compounds this is designated as M/2, for example Ca/2. It has been found that the novel products exhibit superior bactericidal and fungicidal activity over similar products known in the art. In addition to their outstanding fungicidal and bactericidal activity, these products have the added advantage that they are watersoluble because of the presence of the sulfonic acid portion of the molecule and thus can be dissolved in aqueous solutions for use without the necessity for the formation of dispersions and the like. In addition, the compounds exhibit a higher degree of mildew-proofing than the corresponding non-sulfonated derivatives thus providing additional advantages for the products of the invention.

The products of the invention are prepared by initially converting the commercially available 3,5-dibromosalicylic acid to its corresponding acid halide, preferably acid chloride, by reaction with any of the well known halogenating agents such as thionyl chloride, phosphorous trichloride, phosphorus pentachloride, phosphorus oxychloride, sulfuryl chloride, and the like. This reaction is preferably carried out in the presence of an organic solvent including the aromatic hydrocarbons, the aliphatic hydrocarbons and the chlorinated aromatic and aliphatic hydrocarbons. Particularly preferred solvents for this reaction are benzene, toluene, xylene, chlorobenzene, chloroethane and the like. Mixtures may, of course, also be used. The reaction is generally carried out by contacting the reactants in the solvent at a temperature of about 0° to 50° C and then removing the solvent.

The acid chloride recovered from this reaction is then contacted with approximately a stoichiometically equivalent amount of the desired aminobenzensulfonic acid. In this reaction, while equivalent amounts are preferred, an excess of up to 10% by weight of either reactant can be used.

The reaction is preferably carried out in a suitable solvent and preferably nitrogen-containing solvents including the liquid heterocyclics such as pyridine and picoline as well as dimethylformamide, dimethylacetamide and the like. In general, the reaction is conducted at atmospheric pressure and over a temperature range of from about 50°C. to the reflux point of the solvent.

The product formed from this reaction is the free sulfonic acid derivative inasmuch as the sulfonic acid compounds are used as initial reactants. However, for conversion to the desired metal salt of this invention it has been found convenient to isolate the product from an alkali metal solution, usually as the sodium salt, although potassium or lithium salts may also be used if desired. This is conveniently effected by dissolving the resulting product is water in the presence of a sufficient amount of an alkali metal hydroxide such as sodium hydroxide to give an alkaline reaction. Then, the addition of sodium chloride and filtering will yield the sodium salt of the final product.

The product can be converted to other salts of metals which are more insoluble than the sodium salt such as the salts of calcium, magnesium, copper, zinc, etc., as described above by adding to the solution of the sodium salt, a solution of the desired metal in salt form and isolating by filtration or any other convenient manner. These metals are added as soluble salts, and preferably as the chlorides, although others may be used.

While any of the compounds falling within the scope of the above generic formula may be used according to this invention, the following are especially preferred aminobenzenesulfonic acids which may be employed in forming the final products.

Orthanilic acid
Metanilic acid
Sulfanilic acid
4-Amino-1,3-benzenedisulfonic acid
5-Amino-1,3-benzenedisulfonic acid
2-Amino-1,4-benzenedisulfonic acid
5-Bromoorthanilic acid
5-Chloroorthanilic acid
6-Bromometanilic acid
6-Chlorometanilic acid
4,6-Dibromometanilic acid
3-Chlorosulfanilic acid
3-Bromosulfanilic acid
3,5-Dibromosulfanilic acid
4-Amino-5-bromo-1,3-benzenedisulfonic acid
4-Amino-5-chloro-1,3-benzenedisulfonic acid As pointed out above, the compounds of this invention have been found to be eminently suitable as biocidal agents and particularly useful as fungicides and bactericides. For application for the desired use, the compounds being soluble in water, are preferably prepared for use by dissolving about 0.01 up to about 1.0 weight percent in water. Since the products are water soluble it is highly preferred that they be applied from a water solution. The compositions of this invention may be applied in known manner against the fungi and bacteri to be affected and have been found to provide better results than the analogous prior art compounds discussed above.

The products of this invention are effective in the protection of textiles, wood, paper and other cellulosic fibrous materials, from the deleterious action of fungi and other cellulose-destroying organisms. They may be applied in general for the finishing of textiles to reduce mildew deterioration. They may be applied to the foliage of trees and plants for fungus control, in washing apples and oranges and the like, for the inhibition of pathogens, for treating seeds and for the drenching of flats of seedlings and for the prevention of damp-off.

The preservatives may be modified by the addition thereto of adjuvants, such as wetting agents, water repellants, insect repellants, fire retardants, substances which have a synergistic action, or have a desirable action in further protecting or enhancing the value of the treated article.

The carrier employed is a selective material or materials into which the compounds of this invention are incorporated to produce the fungicidal or bactericidal compositions. Since these compounds are water soluble, water is the preferred carrier, but any carrier, such as a solvent in which the compounds are soluble or dispersible, dust, or other material chosen for a particular intended use of the toxicant incorporated therein, may be employed.

The following examples set forth specific embodiments of the invention but it is not to be considered as limited thereto. Parts are by weight unless otherwise indicated.

EXAMPLE I

A. This example illustrates preparation of the compound having the formula:

$$\underset{Br}{\overset{Br\ OH}{\underset{|}{\overset{|}{C_6H_2}}}}-CONH-C_6H_4-SO_3Ca/2$$

212 Grams of 3,5-dribromosalicylic acid, 200 ml, benzene and 100 ml. thionyl chloride are charged into a 1 liter flask equipped with a condenser, stirrer, thermometer and heating mantle. 8 drops of picoline in 40 ml. benzene are added dropwise and then the reaction mixture is stirred at 40 C. for 60 hours. The thionyl chloride and benzene are distilled off under vacuum with a water aspirator. 221 Grams of 3,5-dibromosalicylic acid chloride is obtained.

100 Grams of this product, 200 ml. pyridine and 57 grams of sulfanilic acid are mixed together, heated to reflux and refluxed for 4 hours. The pyridine is then steam distilled off. The charge is cooled to 5°C., filtered, washed with water and oven dried at 40°C.

75 Grams of this product is then slurried with 250 ml. of water, 27 cc. of sodium hydroxide (40% wt./vol.) is added to give an alkaline reaction, it is stirred to solution. 7 Grams of sodium chloride are added, stirred for 15 minutes, cooled to 25°C., filtered and air dried at 80°C.

10 Grams of this product and 60 ml. water are heated to 70 C. and stirred to solution. Then 1.3 grams of calcium chloride dissolved in 50 ml. water is added. The charge is cooled, filtered and dried to give the desired product.

In the following portions of this example, the reaction of A is repeated except that in the last step, different metal salts are added to provide compounds where M is Mg, Cu and Zn. These examples are as follows:

B. Metal salt- MgCl$_2$ Product

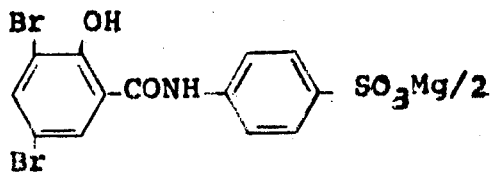

C. Metal salt- CuCl$_2$ Product

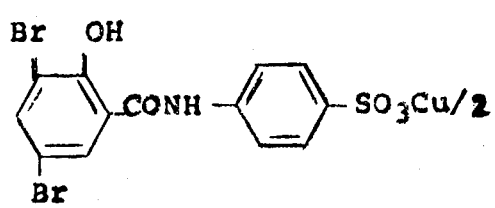

D. Metal salt- ZnCl$_2$ Product

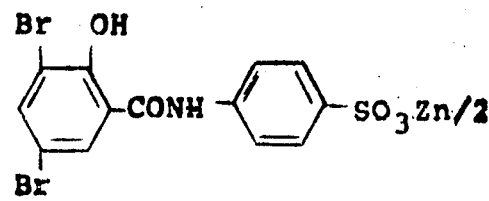

EXAMPLE 2

Application of the product of Example 1.

0.1 Gram of the product of Example 1 is combined with 2 ml. dimethylformamide and this mixture, at 70°C, is poured into 1 liter of water. The proper aliquot of this mixture to give 25 ppm in water is taken for dipping paper and treating cloth according to AATCC test 6205. The test papers are 1½ inch squares of Whatman No. 2 filter paper.

A culture medium is made up consisting of the following:

|  | Grams |
| --- | --- |
| Ammonium nitrate | 3.0 |
| Potassium monohydrateorthophosphate | 2.5 |
| Magnesium sulfate-7H$_2$O | 2.0 |
| Agar | 20.0 |
| Distilled water up to | 1000 |

The pH is adjusted to 6.4–6.8 and the solution is sterilized in an autoclave for 20 min. at 250°F. and 15 lbs. pressure and then cooled.

Scrapings are made from a Petri dish which had been inoculated with chaetomium globosum and incubated for 10 days and stirred into a flask containing 100 ml. distilled water. The chaetomium globosum is admixed with the culture medium employing a transfer loop. Paper, which had previously been dipped in the solution of 4-(3,5-dibromosalicylamido)benzenesulfonic acid, calcium salt, and dried is then dipped into the inoculated agar medium, allowed to dry and maintained under sterile conditions at 80°F.

Paper was treated in similar manner employing an equivalent amount of 3,4',5-tribromosalicylanilide, dissolving 0.1 gm. of the latter in 2 ml. of dimethyl formamide at 70°C., drowning into 1 liter water, then dipping paper into dispersion of 25 ppm. After 24, 48 and 72 hours the paper treated with 4-(3,5-dibromosalicylamido)benzenesulfonic acid, calcium salt showed much less growth than in the case of the 3,4',5-tribromosalicylanilide.

0.1 Gram of the product of Example 1 is combined with 2 ml. dimethylformamide and this mixture, at 70°C, is poured into 1 liter of water. The proper aliquot is taken and made up with 100 ml. water and 8% Tide detergent to give 0.1% o.w.f. of the product. 5 g. cotton cloth is introduced and agitated in the bath for 10 minutes at 120°F. The cloth is removed, rinsed and dried. It is cut into 1½ in. squares, treated with the fungus culture as above and incubated for 24, 48, 72 hours. The cloth treated with this product showed much less growth than in the case of 3,4',5-tribromosalicylanilide.

EXAMPLE 3

Preparation and application of the compound having the formula:

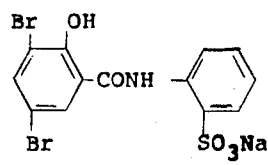

100 grams of 3,5-dibromosalicylic acid chloride, 200 ml. pyridine and 57 grams of orthanilic acid are mixed together, heated to reflux and refluxed for four hours. The pyridine is then steam distilled off. The charge is cooled to 5°C., filtered, washed with water and oven dried at 40°C.

75 Grams of this product is then slurried with 250 ml. water. 27 cc. of sodium hydroxide is added to give an alkaline solution and it is stirred to solution, 7 grams of sodium chloride are added, stirred for 15 minutes, cooled to 25°C., filtered and air dried at 80°C.

Paper and cotton cloth treated according to the manner of Example 2 showed inhibition of mildew in the treated paper and cotton in contrast to the mildew which proliferated in untreated paper and cotton.

The sodium salt of this example is converted into the calcium salt in the manner of Example 1. Paper and cotton cloth treated in the manner of Example 1 showed less mildew than in the case of paper and cotton treated in similar manner with 3,4',5-tribromosalicylanilide, and especially untreated paper and cotton.

EXAMPLE 4

Preparation and application of the compound having the formula:

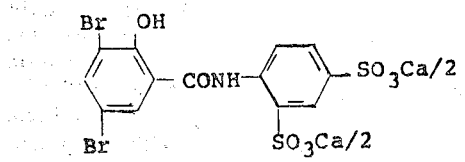

100 Grams of 3,5-dibromosalicyl acid chloride, 200 ml. pyridine and 84 grams of 4-amino-1,3-benzenedisulfonic acid are combined, heated to reflux and refluxed for 4 hours. The pyridine is then steam distilled off. The charge is cooled to 5°C., filtered, washed with water and oven dried at 40°C.

75 Grams of this product are slurried with 250 ml. water. 27 cc. Sodium hydroxide is added to give an alkaline reaction, it is stirred to solution, 7 grams of sodium chloride are added, stirred for 15 minutes, cooled to 25°C., filtered and air dried at 80°C.

10 Grams of this product and 60 ml. water are then heated to 70°C. and stirred to solution, 2.6 grams of calcium chloride dissolved in 100 ml. water are added, the charge is cooled, filtered and dried to give the desired product.

Treatment of paper and cotton pieces as described in Example 2 showed less mildew than in the cases of paper and cotton treated in similar manner with 3,4',5-tribromosalicylanilide and much less than in the cases of untreated paper and cloth.

EXAMPLE 5

Preparation and application of the compound having the formula:

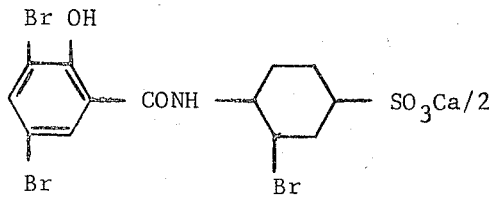

In the manner of Example 1, 100 grams 3,5-dibromosalicyclic acid chloride is reacted with 84 grams 3-bromosulfanilic acid to product 3-bromo-4-(3,5-dibromosalicylamido)benzene sulfonic acid, which is then converted to the sodium salt, and then to the calcium salt.

Paper and cotton treated with the above compound of this invention in the manner of Example 2 showed less mildew than a paper and cotton correspondingly treated with 3,4',5-tribromosalicylanilide, and considerably less mildew than untreated paper and cotton.

The invention has been described with reference to certain preferred embodiments. However, as obvious variations thereon will become apparent to those skilled in the art, the invention is not to be considered as limited thereto.

What is claimed is:

1. Compounds of the following general formula:

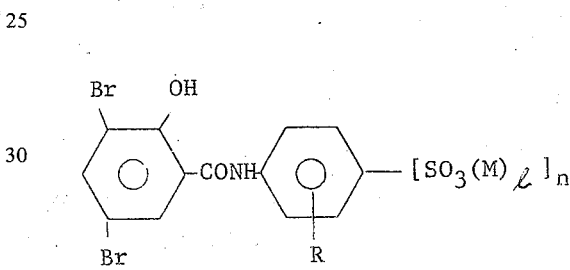

wherein R is hydrogen or halogen, n is a whole number of 1 or 2, $l$ is ½ or 1 and M is selected from the group consisting of alkali metals, alkaline earth metals, copper and zinc.

2. A compound according to claim 1 wherein R is hydrogen, chlorine or bromine.

3. A compound according to claim 1 wherein R is hydrogen, n is 1 and M is sodium l is 1.

4. A compound according to claim 1 wherein R is hydrogen, n is 1 and M is calcium l is 1/2.

5. A compound according to claim 1 wherein R is hydrogen, n is 1 and M is magnesium l is 1/2.

6. A compound according to claim 1 wherein R is hydrogen, n is 1 and M is copper l is 1/2.

7. A compound according to claim 1 wherein R is hydrogen, n is 1 and M is zinc l is 1/2.

8. A compound according to claim 1 wherein R is bromine, n is 1 and M is sodium, calcium, magnesium, copper or zinc.

9. A compound according to claim 1 wherein n is 2.

* * * * *